United States Patent
Bonda et al.

(12)
(10) Patent No.: US 6,180,091 B1
(45) Date of Patent: Jan. 30, 2001

(54) COMPOSITIONS CONTAINING DIESTERS OR POLYESTERS OF NAPHTHALENE DICARBOXYLIC ACID AND METHODS FOR IMPARTING HAIR GLOSS AND TO PROVIDE HAIR COLOR AND HAIR DYE STABILIZATION

(75) Inventors: Craig A. Bonda, Wheaton; Peter J. Marinelli, Bartlett; Yin Z. Hessefort, Naperville; Jagdish Trivedi, Woodridge; Gary Wentworth, Chicago, all of IL (US)

(73) Assignee: The C. P. Hall Company, Chicago, IL (US)

( * ) Notice: Under 35 U.S.C. 154(b), the term of this patent shall be extended for 0 days.

(21) Appl. No.: 09/490,229

(22) Filed: Jan. 24, 2000

Related U.S. Application Data (63) Continuation of application No. 09/391,766, filed on Sep. 8, 1999, now Pat. No. 6,129,909, which is a continuation-in-part of application No. 09/276,051, filed on Mar. 25, 1999, now Pat. No. 5,993,789.

(51) Int. Cl.[7] .............................. A61K 7/06; A61K 7/42; A61K 7/00
(52) U.S. Cl. .......................... 424/70.1; 424/59; 424/70.6; 424/400; 424/401
(58) Field of Search .......................... 424/59, 70.1, 70.6, 424/400, 401

(56) References Cited

U.S. PATENT DOCUMENTS

| | | | |
|---|---|---|---|
| 4,308,328 | 12/1981 | Salyer et al. | 430/17 |
| 4,387,089 | 6/1983 | De Polo | 424/59 |
| 4,489,057 | 12/1984 | Welters et al. | 424/47 |

(List continued on next page.)

FOREIGN PATENT DOCUMENTS

| | | |
|---|---|---|
| 04221330 | 8/1992 | (JP) . |
| 99/24256 | 5/1999 | (WO) . |

OTHER PUBLICATIONS

"Photostable Cosmetic Light Screening Composition", Author: Anon. Organization, UK Publication Source, Research Disclosure (1999), 418(Feb.), P175 (No. 41803). Identifier–CODEN RSDSBB ISSN 0374–4363Publisher Kenneth Mason Publications Ltd. Patent Information.

(List continued on next page.)

*Primary Examiner*—Shelley A. Dodson
(74) *Attorney, Agent, or Firm*—Marshall, O'Toole, Gerstein, Murray & Borun

(57) ABSTRACT

A hair-treating composition containing a diester or polyester of a naphthalene dicarboxylic acid having compound formula (I) (II) or (III), or mixtures; for imparting gloss and/or hair color stabilization:

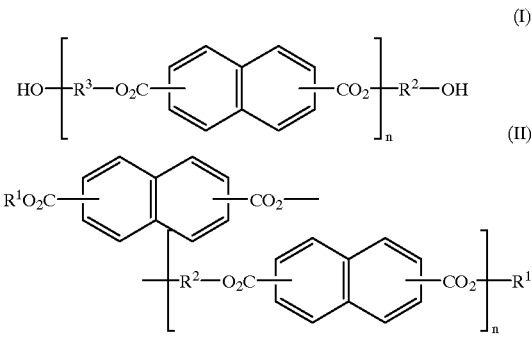

wherein each $R^1$, same or different, is an alkyl group having 1 to 22 carbon atoms, a diol having the structure $HO-R^2-OH$, or a polyglycol having the structure $HO-R^3-(-O-R^2-)_m-OH$, wherein $R^2$ and $R^3$, same or different, are each an allylene group, straight chain or branched, having 1 to 6 carbon atoms, and wherein m and n are each 1 to about 100, or a mixture thereof. These diesters and polyesters of formula (I) or (II) are quite effective in stabilizing the dibenzoylmethane derivative UV-A filter compounds making them more effective, and effective for longer periods of time.

20 Claims, 9 Drawing Sheets

U.S. PATENT DOCUMENTS

| | | | |
|---|---|---|---|
| 4,562,067 | 12/1985 | Hopp et al. | 424/59 |
| 4,990,690 | 2/1991 | Onda et al. | 568/814 |
| 5,670,140 | 9/1997 | Deflandre et al. | 424/59 |
| 5,783,173 | 7/1998 | Bonda et al. | 424/59 |
| 5,788,954 | 8/1998 | Bondo et al. | 424/59 |
| 5,849,273 | 12/1998 | Bondo et al. | 424/59 |
| 5,882,634 | 3/1999 | Allard et al. | 424/59 |
| 5,976,513 | 11/1999 | Robinson | 424/59 |

OTHER PUBLICATIONS

"Polyester And Copolyester Sheeting, Film And Structured Products Stabilized Against Degradation By Sunlight Or Other UV Light Sources", Author: Anon. Organization, Research Disclosure (1994), (Nov.), P601 (No. 36708).

STN, File Supplier, Karlsruhe, DE, File Chemical Abstracts, vol. 130, AN=158258 see the abstract XP002126186 & Research Disclosure, No. 418003, Feb. 10, 1999, p. 175 UK the whole document.

COMPOSITIONS CONTAINING DIESTERS OR POLYESTERS OF NAPHTHALENE DICARBOXYLIC ACID AND METHODS FOR IMPARTING HAIR GLOSS AND TO PROVIDE HAIR COLOR AND HAIR DYE STABILIZATION

CROSS-REFERENCE TO RELATED APPLICATION

This application is a continuation of application Ser. No. 09/391,766 filed Sep. 8, 1999, U.S. Pat. No. 6,129,909, which is a continuation-in-part of copending application Ser. No. 09/276,051 filed Mar. 25, 1999 U.S. Pat. No. 5,993,789.

FIELD OF THE INVENTION

The present invention is directed to compositions for topical application to hair to impart gloss and to stabilize natural and/or synthetic hair color. More particularly, the present invention is directed to the use of diesters and/or polyesters of a naphthalene dicarboxylic acid that are surprisingly effective in imparting gloss and for stabilizing hair color against fading. The diesters and polyesters of naphthalene dicarboxylic acid stabilize natural hair color and hair dyes and impart gloss to the hair. In addition, as described in more detail in the parent application, now U.S. Pat. No. 5,993,789, the composition absorbs UV radiation.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles.

Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or PARSOL® MCX, having an ethyl radical extending from the 2 position of the hexyl long chain backbone; oxybenzone; and octyl salicylate.

The UV-A filters most commonly used in commercial sunscreen compositions are the dibenzoylmethane derivatives, particularly 4-(1,1-dimethylethyl)4'-methoxydibenzoylmethane (PARSOL® 1789), and 4-isopropyl dibenzoylmethane (EUSOLEX 8020). Other dibenzoylmethane derivatives described as UV-A filters are disclosed in U.S. Pat. Nos. 4,489,057; 4,387,089 and 4,562,067 and 5,670,140, hereby incorporated by reference. It is also well known that the above described and most commonly used UV-A filters, particularly the dibenzoylmethane derivatives, such as PARSOL® 1789, suffer in photochemical stability when used alone or in combination with the above-described most commercially used UV-B filters. Accordingly, when used alone or when combined with a UV-B filter, such as 2-ethylhexyl paramethoxycinnamate (PARSOL® MCX), oxybenzone and/or octyl salicylate, the PARSOL® 1789 becomes less photochemically stable necessitating repeated, frequent coatings over the skin for sufficient UV radiation protection.

In accordance with one embodiment of the present invention, it has been found, quite surprisingly, that by including a diester and/or polyester of one or more naphthalene dicarboxylic acids of formula (I), into a cosmetic sunscreen formulation containing a UV-A dibenzyolmethane derivative, particularly PARSOL® 1789, and/or 4-isopropyl dibenzoylmethane (EUSOLEX 8020), the dibenzyolmethane derivative is photochemically stabilized so that the dibenzyolmethane derivative-containing sunscreen composition with or without additional sunscreen agents, such as oxybenzone and/or octyl methoxycinnamate (ESCALOL 567), is more effective for filtering out UV-A radiation; the composition filters more UV-A radiation for longer periods of time; and, therefore, the sunscreen formulation need not be applied to the skin as frequently while maintaining effective skin protection against UV-A radiation.

Figure 9:
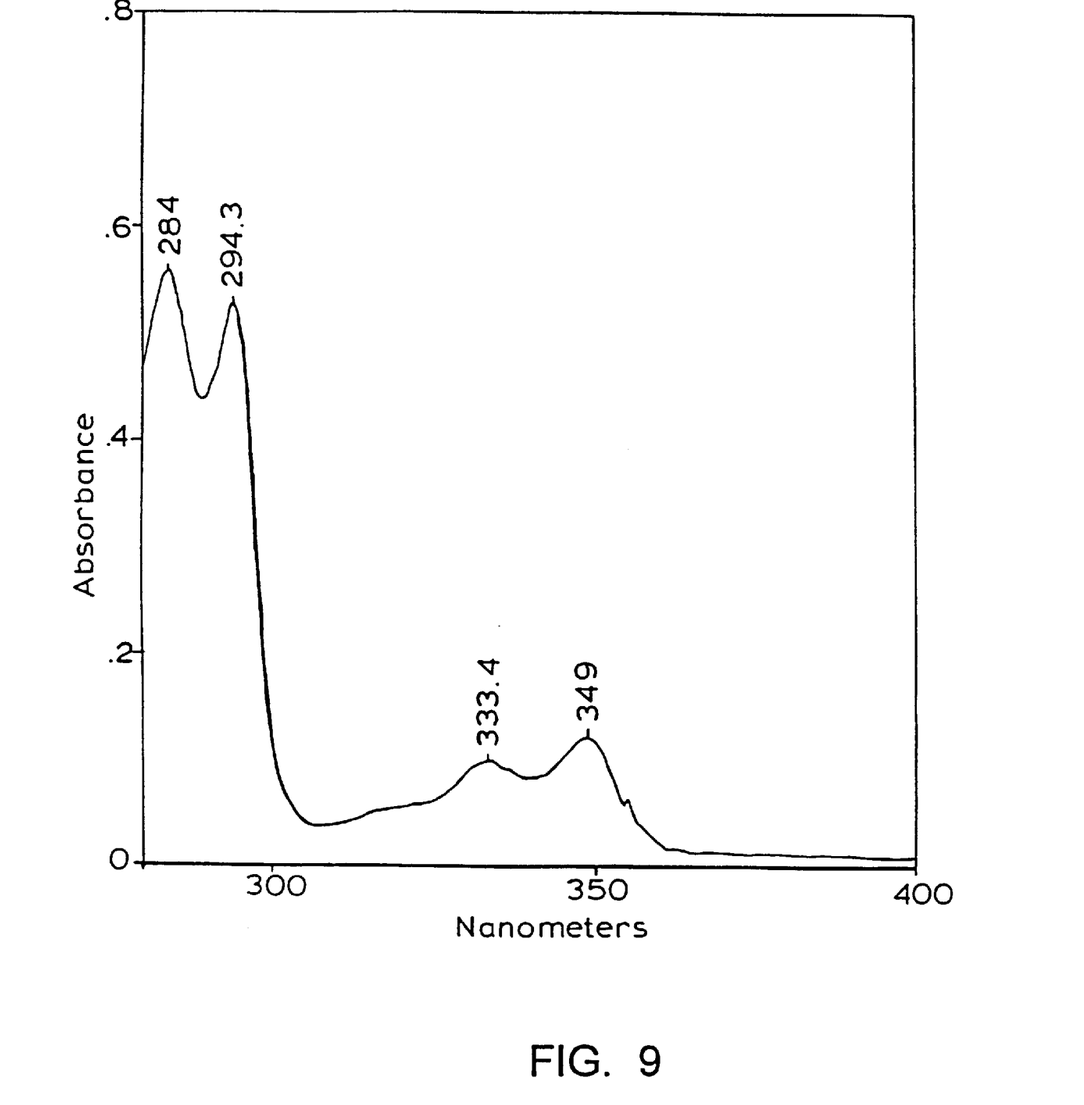
FIG. 9 is a graph showing the UV absorbance of the naphthalic dicarboxylic acid of Example 1 at 17.5 ppm in tetrahydrofuran (THF).

In accordance with another important advantage of the present invention, it has been found that the diesters and polyesters of naphthalene dicarboxylic acids can also absorb UV light in the most damaging range of about 280–300 nm, especially over the 280 and 295 nm wavelength absorbance peaks shown in FIG. 9.

By the addition of UV-B filter compounds, such as octyl methoxycinnamate, octyl salicylate, and/or oxybenzone, the compositions of the present invention can maintain surprisingly effective hair color protection and can protect against UV radiation both in the UV-A and UV-B range, with or without common sunscreen additives, such as octocrylene, and/or titanium dioxide. The composition reaches a surprisingly high SPF without solid additives, such as titanium dioxide, thereby providing an exceptionally elegant feel that can be applied easily in a continuous coating for complete coverage and sunscreen protection. In the preferred compositions, the ratio of UV-A to UV-B filter compounds is in the range of about 0.1:1 to about 3:1, preferably about 0.1:1 to about 0.5:1, most preferably about 0.3:1 to about 0.5:1. Quite surprisingly, the preferred compositions of the present invention achieve unexpectedly high SPF, e.g., higher than SPF 12 in one preferred composition, and higher than SPF 20 in another preferred composition, with the addition of surprisingly low amounts of other UV-B and UV-A filters to the PARSOL 1789, and without solid blocking compounds, such as $TiO_2$.

In accordance with another embodiment of the present invention, the diesters and polyesters of naphthalene dicarboxylic acid, of the present invention, impart gloss to hair, and/or stabilize hair color against fading, particularly for hair containing a synthetic dye.

SUMMARY OF THE INVENTION

In brief, the present invention is directed to gloss-imparting and/or hair color protecting compounds comprising a diester and/or polyester of a naphthalene dicarboxylic acid, while providing UV absorption.

The active gloss-imparting and/or hair color stabilizing compounds of the present invention are diesters and polyesters of a naphthalene dicarboxylic acid. The diesters and polyesters are reaction products of (a) a naphthalene dicarboxylic acid having the structure:

and (b) an alcohol having the structure $R^1$—OH, or a diol having the structure HO—$R^2$—OH, or a polyglycol having the structure HO—$R^3$—(—O—$R^2$—)$_m$—OH, wherein $R^1$ is an alkyl group, straight chain or branched, having 1 to 22 carbon atoms, $R^2$ and $R^3$, same or different, are each an alkylene group, having 1 to 6 carbon atoms, and wherein m and n are each 1 to about 100, preferably 1 to about 10, more preferably 2 to about 7, or a mixture thereof.

A diester of the present invention has the structure (III):

wherein $R^1$ is as defined above.

The diesters and polyesters of naphthalene dicarboxylic acids of the present invention have the general formula (I):

wherein $R^2$ and $R^3$, same or different, are each an alkylene group having 1 to 6 carbon atoms, and n=1 to about 100, preferably 1 to about 10, more preferably 2 to about 7.

Alternatively, the hair color stabilizing diesters and polyesters of the present invention can be end-capped with an alcohol or an acid. The end-capped polyesters have the structural formula (II):

wherein $R^1$ and $R^2$ and n are as defined above, with reference to formula (I). The two $R^1$s in formula (II) may be the same or different.

The preferred diesters and polyesters of the present invention have a weight average molecular weight of about 244 to about 4000, and more preferably about 450 to about 1500. To achieve the full advantage of the present invention, the diester or polyester has a weight average molecular weight of about 500 to about 1000.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^1$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

The glycol or polyglycol can be, for example, ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

Surprisingly, it has been found that these diesters and polyesters of naphthalene dicarboxylic acids are quite effective in imparting hair gloss and preserving a desired natural or dyed hair color, while providing the hair with sunscreen protection, when contained in a composition in an amount of at least about 0.1% by weight, up to about 20% by weight, preferably about 0.2% to 10% by weight, more preferably about 0.5% to 10% by weight.

Accordingly, one aspect of the present invention is to provide a composition that includes a diester or polyester of one or more naphthalene dicarboxylic acids as a hair gloss-imparting compound, and as a hair color preserving compound, said naphthalene dicarboxylic acid diester/polyester compounds having formula (I) or (II).

Another aspect of the present invention is to provide a composition for application to human hair that photochemically stabilizes dibenzoylmethane derivatives, particularly PARSOL® 1789, and capable of increasing the sunscreen protection factor (SPF) achievable for sunscreen compositions containing the dibenzoylmethane derivatives.

Another aspect of the present invention is to provide an improved, stable composition containing a diester and/or polyester of a naphthalene dicarboxylic acid that increases the effectiveness of dibenzoylmethane derivative sunscreen compounds, particularly 4-(1,1-dimethylethyl)-4'-methoxydibenzoylmethane (PARSOL® 1789), in SPF and in duration, for protection of human hair.

Another aspect of the present invention is to provide a stable, broad spectrum sunscreen composition for topical application to human hair that has a SPF of at least 12 and provides substantial protection against the full range of solar UV radiation (280–400 nm), including about 4–15% by weight of an ester and/or polyester of naphthalene dicarboxylic acid, and contains less than 7% and preferably less than 6.1% of sunscreen composition additives selected from the group oxybenzone and avobenzone (PARSOL 1789).

Still another aspect of the present invention is to provide a moisturizing composition for topical application to human hair that provides an SPF of at least 20, including about 4–15% by weight of an ester and/or polyester of naphthalene dicarboxylic acid.

The above and other aspects and advantages of the present invention will become more apparent from the following detailed description of the preferred embodiments, taken in conjunction with the drawings.

DETAILED DESCRIPTION OF THE PREFERRED EMBODIMENTS

The preferred compositions of the present invention include, optionally, about 0.5% to about 5%, preferably about 0.5% to about 3% of a dibenzoylmethane derivative UV-A filter compound, such as 4-(1,1-dimethylethyl)-4'-methoxy-dibenzoylmethane (PARSOL® 1789) and about 1% to about 10% by weight of a diester and/or polyester of one or more naphthalene dicarboxylic acid photostabilizer/solubilizer for the dibenzoylmethane derivative, having formula (I) or (II).

(I)

(II)

wherein each $R^1$, same or different, is an alkyl group having 1 to 22 carbon atoms, or a diol having the structure $HO-R^2-OH$, or a polyglycol having the structure $HO-R^3-(-O-R^2-)_m-OH$, and, wherein $R^2$ and $R^3$, same or different, are each an alkylene group, straight chain or branched, having 1 to 6 carbon atoms, wherein m and n are each 1 to about 100, preferably 1 to about 10, more preferably 2 to about 7, or a mixture thereof.

The compounds of formula (I) and (II) are well known for other purposes.

EXAMPLES

Example 1

The photostabilizing effect of a polyester of 2,6-naphthalene dicarboxylic acid and tripropylene glycol with a 2-butyloctanol terminator was determined as follows. First, the following formulations containing 1% PARSOL® 1789 were prepared in the usual way by dissolving the PARSOL® 1789 in the oily phase and premixing the water phase, then emulsifying the oil by adding it to the water phase:

| Ingredient | Formula A (Standard) | Formula B | Formula C | Function |
|---|---|---|---|---|
| hexyldecyl benzoate & butyloctyl benzoate | 7.50% | 7.50% | 7.50% | emollient, solvent |
| isopropyl myristate | 5.00% | 5.00% | 1.00% | co-solvent |
| avobenzone | 1.00% | 1.00% | 1.00% | UV-A sunscreen |
| myristyl myristate | 4.00% | 0.00% | 0.00% | bodying agent |
| polyester of 2,6-naphthalene dicarboxylic acid | 0.00% | 4.00% | 8.00% | photo-stabilizer |
| sorbitan oleate | 0.20% | 0.20% | 0.20% | particle size reducer |
| dimethicone copolyol | 0.10% | 0.10% | 0.10% | lubricant |
| carbomer | 0.20% | 0.20% | 0.20% | thickener, stabilizer |
| acrylates/C10–30 alkyl acrylates crosspolymer | 0.25% | 0.25% | 0.25% | emulsifier |
| deionized water | Q.S. | Q.S. | Q.S. | solvent, carrier |
| disodium EDTA | 0.05% | 0.05% | 0.05% | chelator |
| hydroxypropyl-methylcellulose | 0.20% | 0.20% | 0.20% | film former |
| glycerin | 4.00% | 4.00% | 4.00% | humectant |
| butylene glycol | 2.00% | 2.00% | 2.00% | humectant, solvent |
| phenoxyethanol & parabens | 0.50% | 0.50% | 0.50% | preservative |
| triethanolamine | 0.45% | 0.45% | 0.45% | neutralizer |

The photostability of the PARSOL® 1789 was determined by spreading measured amounts of the emulsions on 5 cm square slides of Vitro-skin, then irradiating the slides with a solar simulator. Absorbance measurements in the UV-A range (315–380 nm) were taken by a Labsphere UV Transmittance Analyzer before and after irradiation and the results compared.

Figure 1:
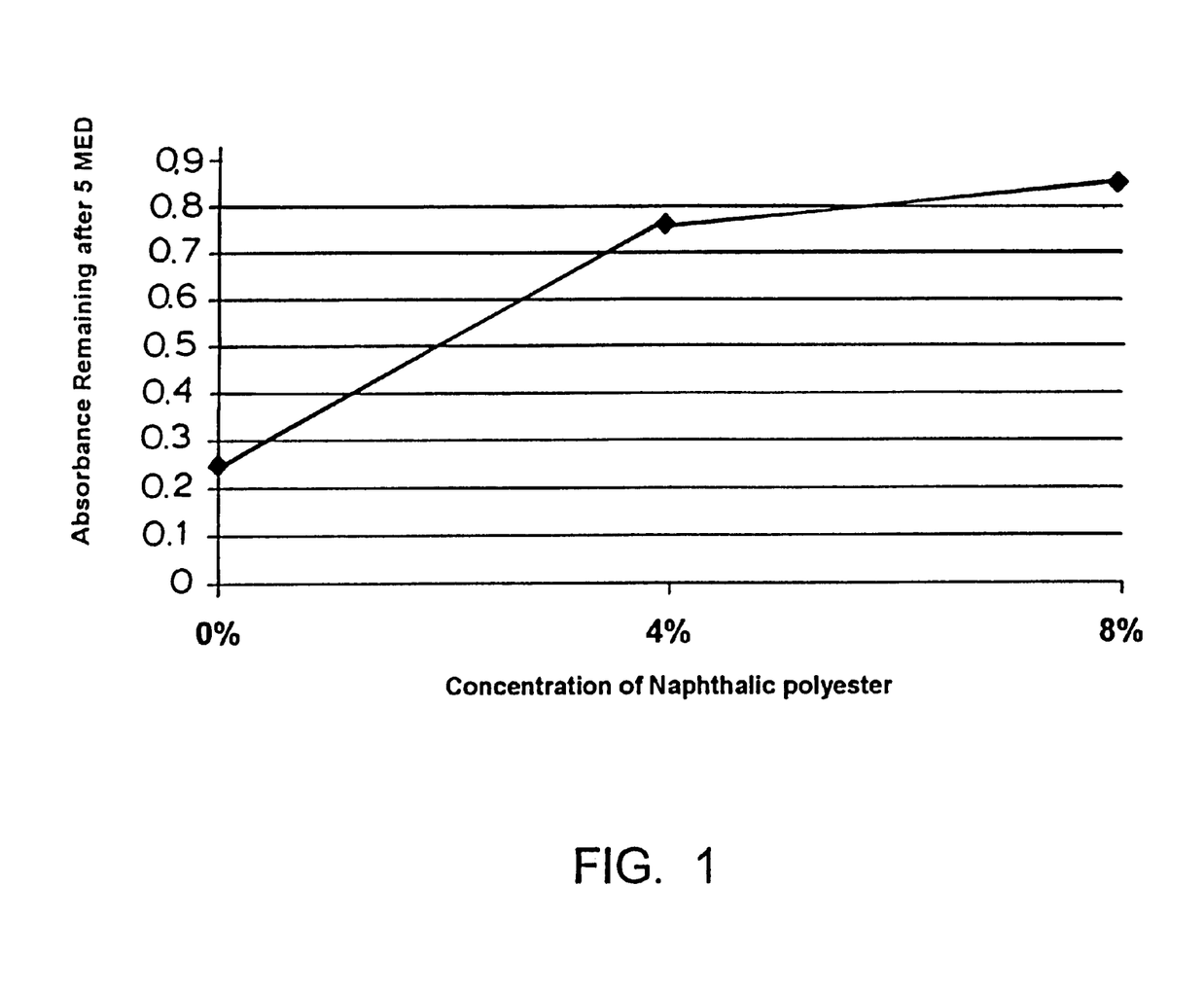
FIG. 1 is a graph showing the photostability of PARSOL® 1789 or 4-(1,1-dimethylethyl)-4'- methoxydibenzoylmethane as a function of concentration of the naphthalene dicarboxylic acid ester photostabilizers of the present invention.
Figure 2:
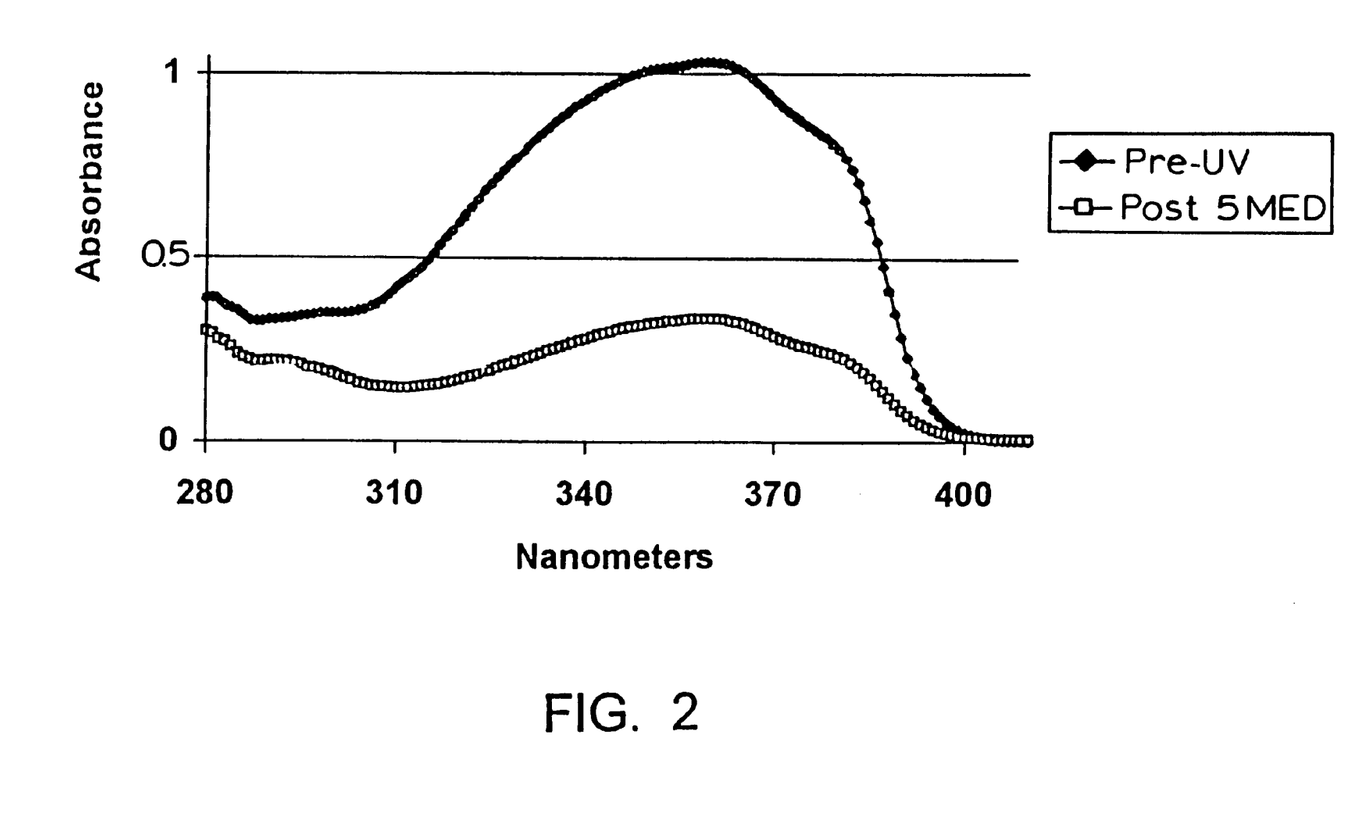
FIG. 2 is a graph showing the photostability (photoinstability) or UV absorbance capability, of a sunscreen composition containing 1% by weight avobenzone when subjected to ultraviolet light of varying wavelengths.
Figure 3:
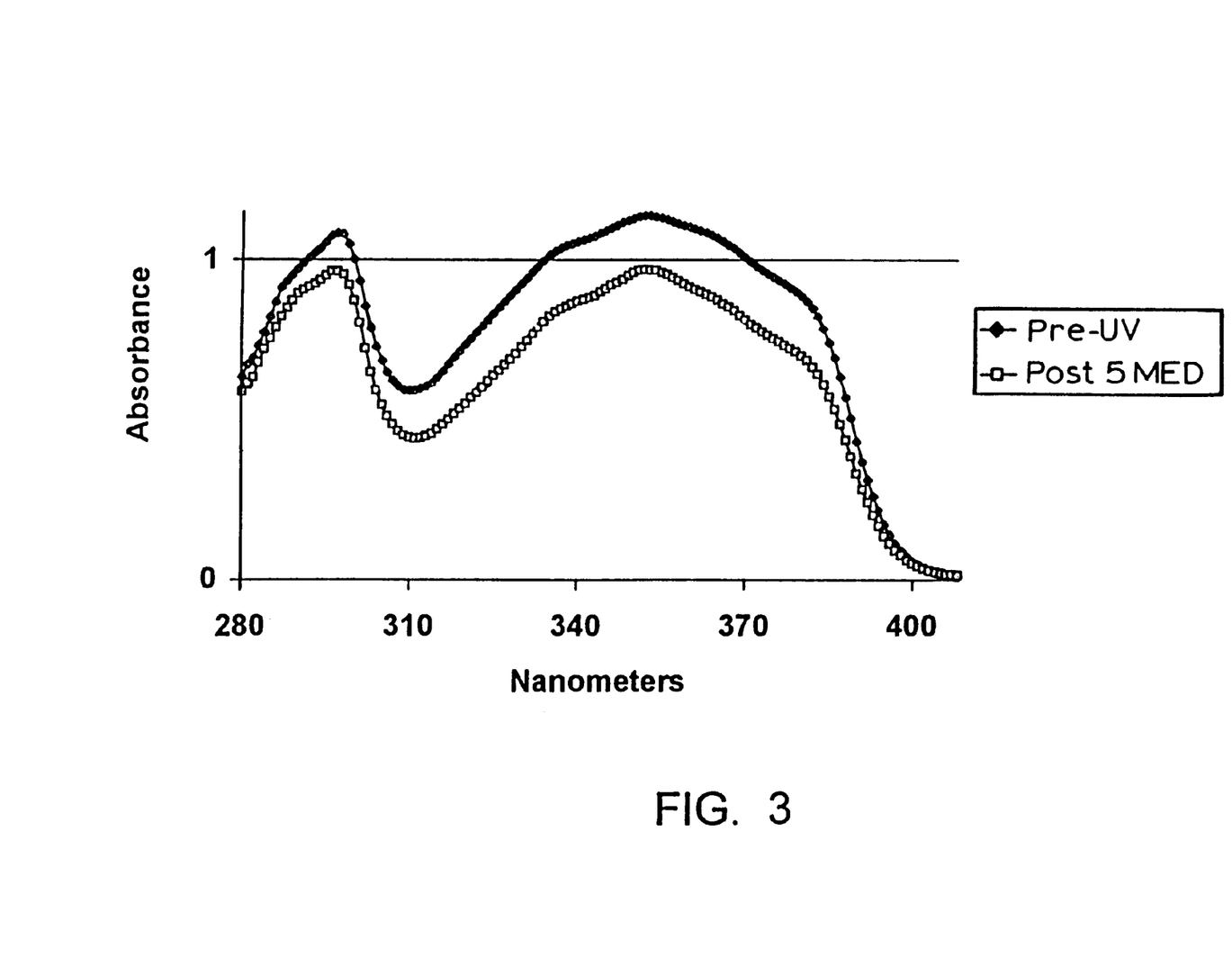
FIG. 3 is a graph showing photostability, or UV absorbance capability, of a sunscreen compositing containing 1% by weight avobenzone when stabilized with 4% by weight of one of the naphthalene dicarboxylic acid polyesters of the present invention.
Figure 4:
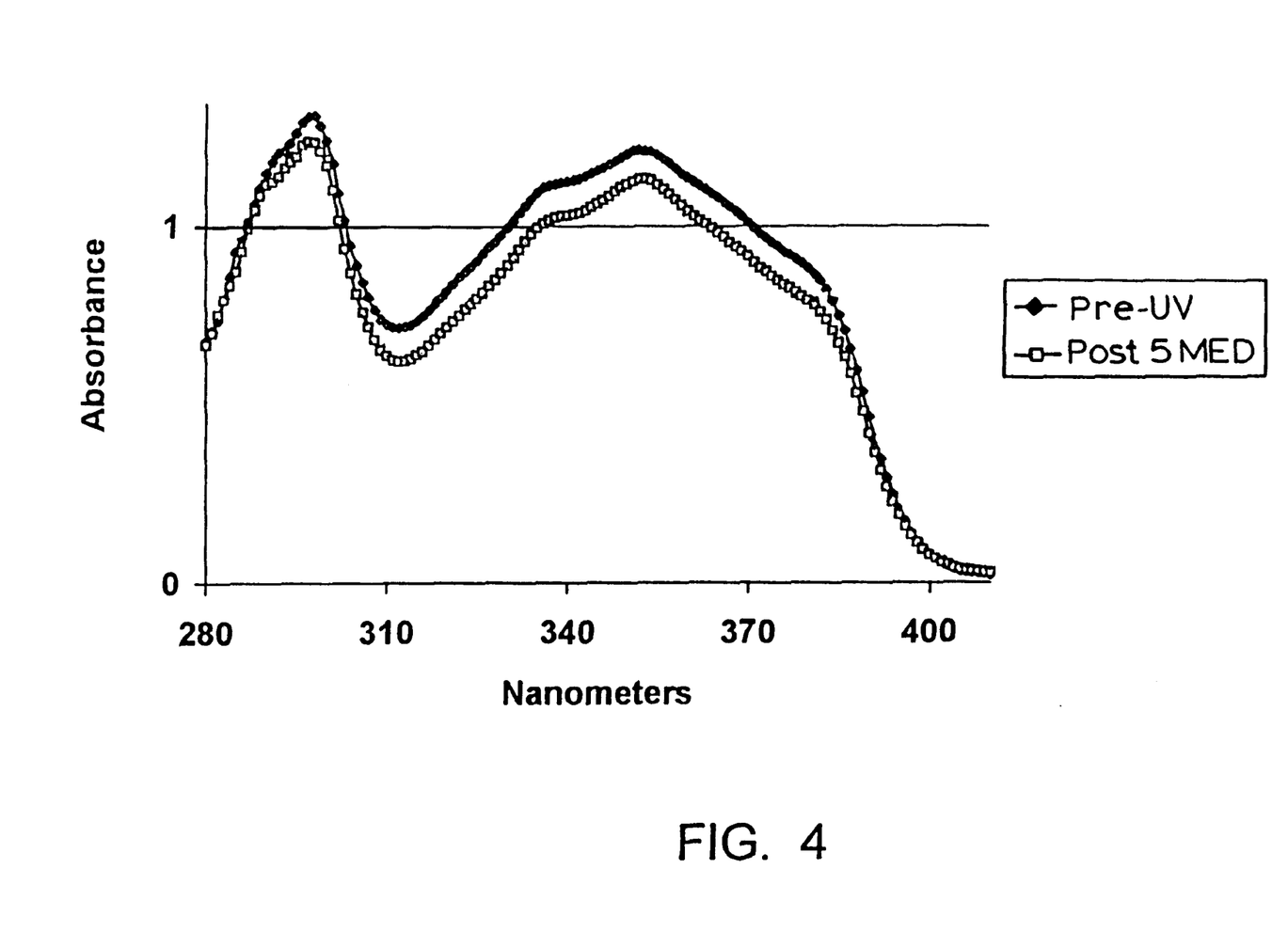
FIG. 4 is a graph showing photostability, or UV absorbance capability, of a sunscreen composition containing 1% by weight avobenzone when stabilized with 8% by weight of one of the naphthalene dicarboxylic acid polyesters of the present invention.
Figure 5:
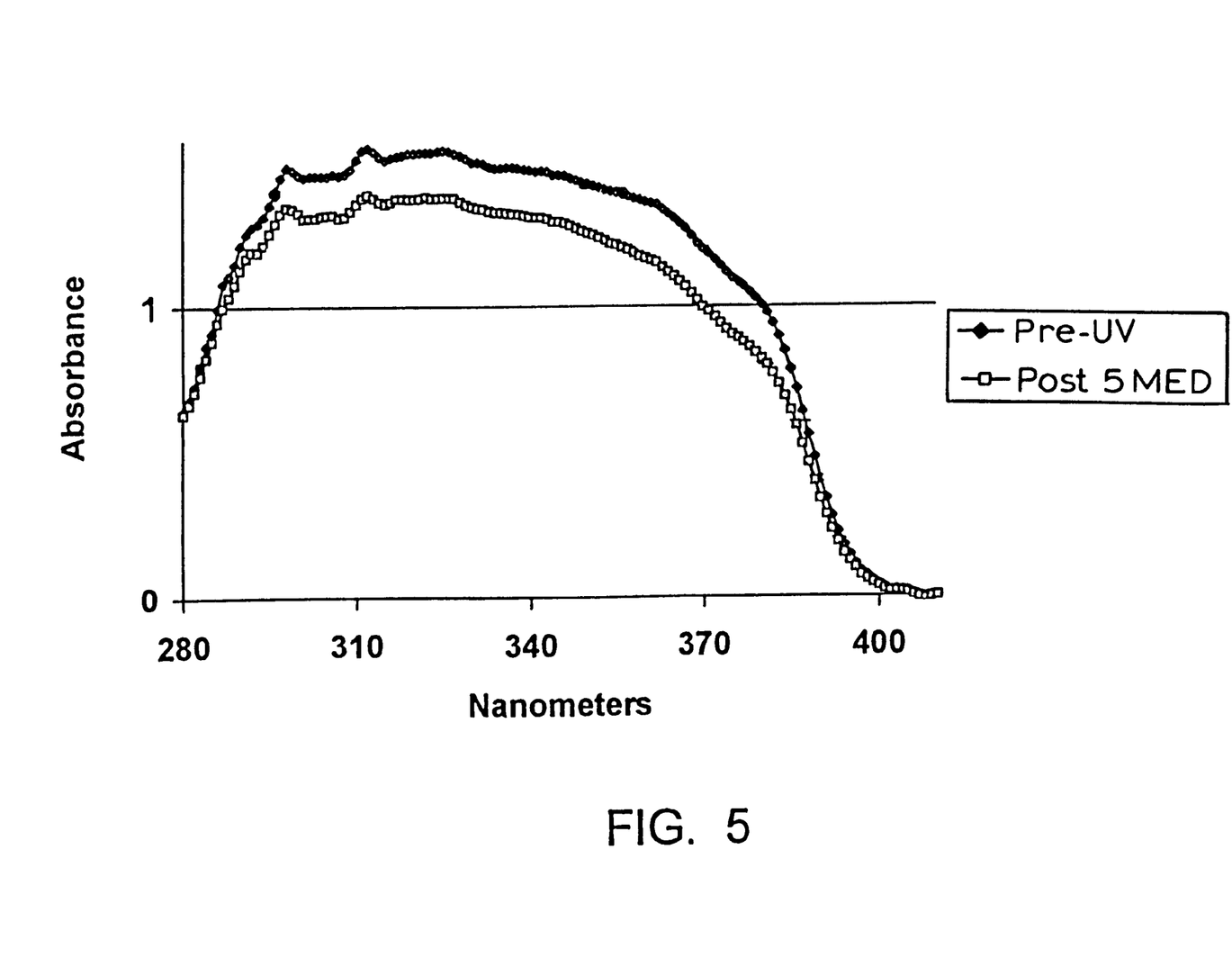
FIG. 5 is a graph showing the photostability of a sunscreen composition containing 3% by weight oxybenzone/1% by weight avobenzone, without a photostabilizer of the present invention.
Figure 6:
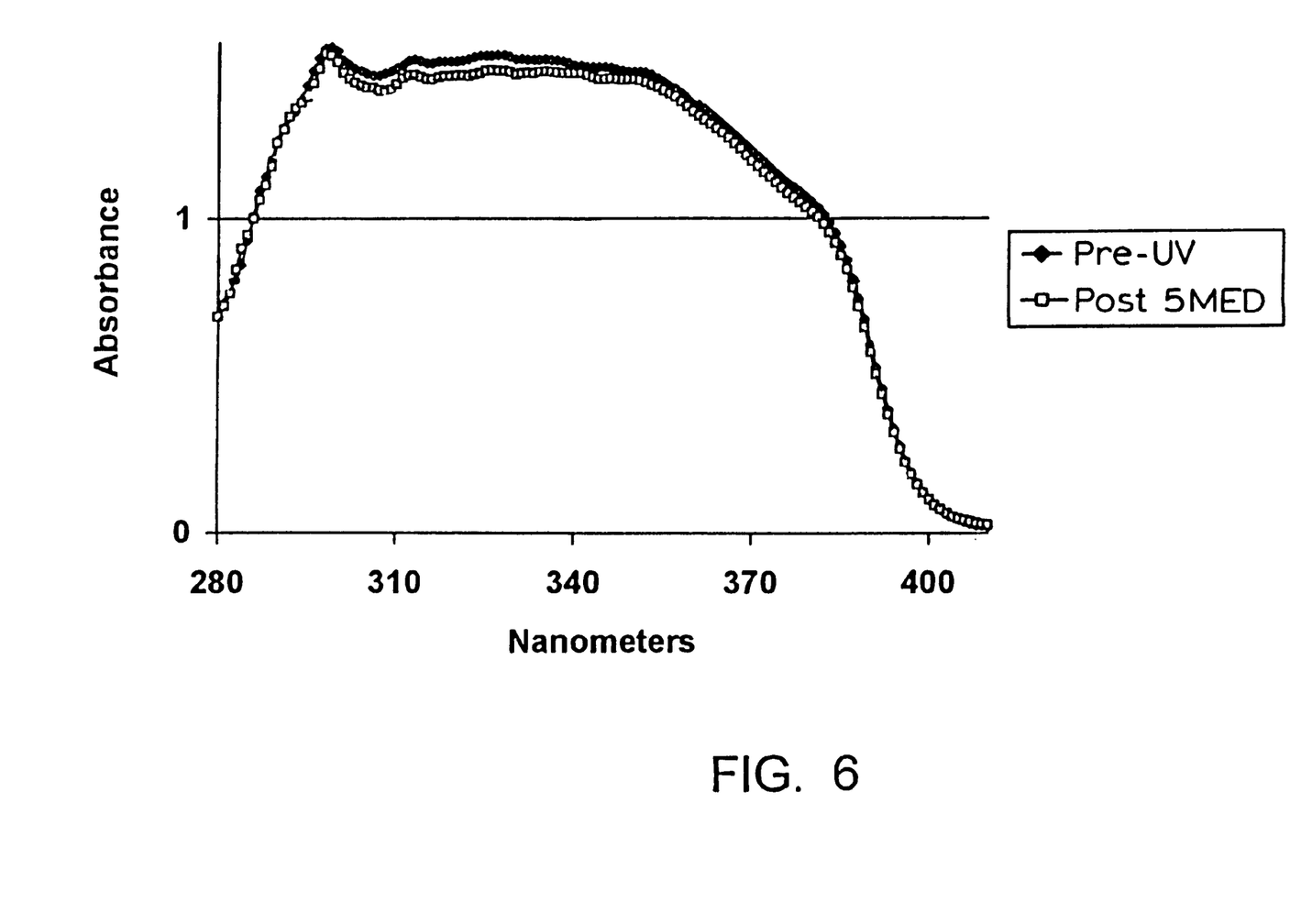
FIG. 6 is a graph showing the photostability of a sunscreen composition containing 3% by weight oxybenzone/1% by weight avobenzone, and 8% by weight of one of the naphthalene dicarboxylic acid polyester photostabilizers of the present invention.
Figure 7:
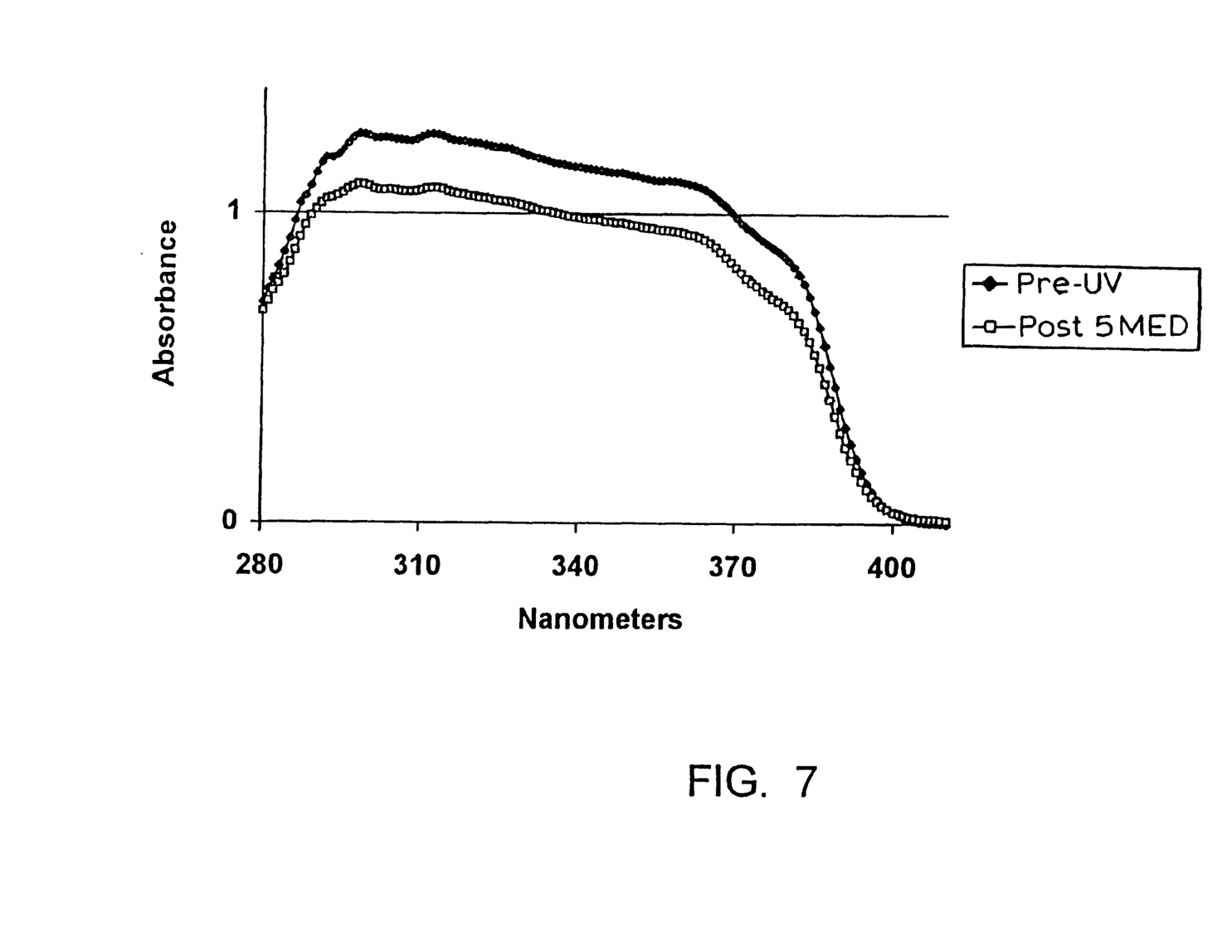
FIG. 7 is a graph showing the photostability of a sunscreen composition containing 1% by weight avobenzone and 4% by weight of an octocrylene photostabilizer.
Figure 8:
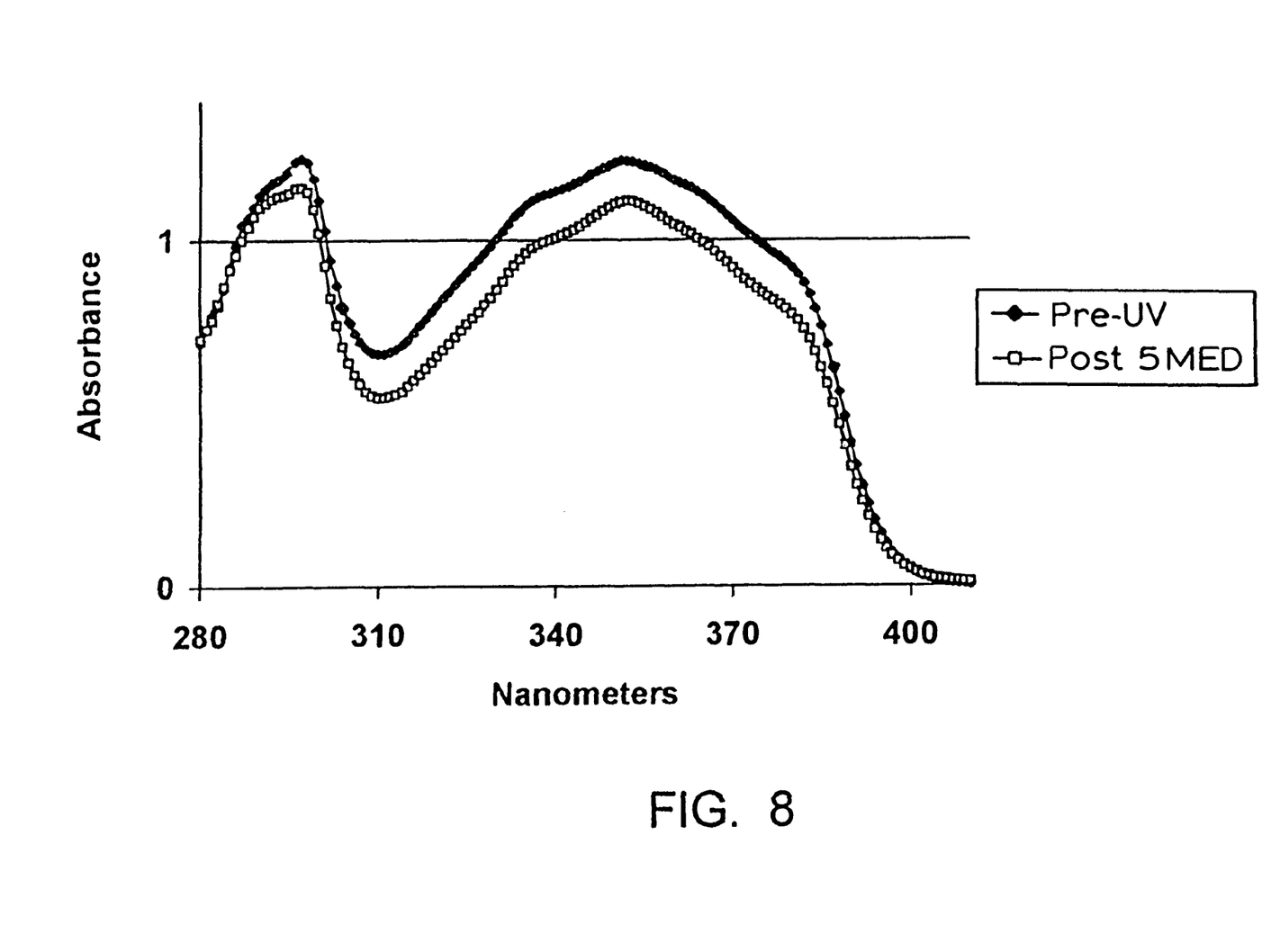
FIG. 8 is a graph showing the photostability of a sunscreen composition containing 1% by weight avobenzone and 4% by weight of an oligomer (MW=1500) of a naphthalene dicarboxylic acid ester of the present invention.

After irradiation with 5 MED (minimal erythermal dose), the loss of UV-A absorbance by the PARSOL® 1789 was considerably lower in the formulations containing the PARSOL® 1789 in combination with 4% and 8% of the naphthalene dicarboxylic polymer when compared to the formulation containing the PARSOL® 1789 alone (compare FIGS. 2, 3 and 4). Further, the loss of absorbance in the UV-A range is reduced in a manner related to the concentration of the naphthalene dicarboxylic polymer, as can be seen in the graph of FIG. 1.

Example 2

The photostabilizing effect of a polyester of 2,6-naphthalene dicarboxylic acid, tripropylene glycol, and diethylene glycol with a 2-ethylhexanol terminator was compared to octocrylene, a well known photostabilizer for PARSOL® 1789. The following formulations were prepared in the usual manner, each containing 1% PARSOL® 1789 and 4% of either octocrylene or a polyester of 2,6-naphthalene dicarboxylic acid:

| Ingredient | Formula A | Formula B | Function |
|---|---|---|---|
| hexyldecyl benzoate & butyloctyl benzoate | 7.50% | 7.50% | emollient, solvent |
| isopropyl myristate | 5.00% | 5.00% | co-solvent |
| avobenzone | 1.00% | 1.00% | UV-A sunscreen |
| octocrylene | 4.00% | 0.00% | UV-B/UV-A sunscreen |
| polyester of 2,6-naphthalene dicarboxylic acid | 0.00% | 4.00% | photostabilizer |
| sorbitan oleate | 0.20% | 0.20% | particle size reducer |
| dimethicone copolyol | 0.10% | 0.10% | lubricant |
| carbomer | 0.20% | 0.20% | thickener, stabilizer |
| acrylates/C10–30 alkyl acrylates crosspolymer | 0.25% | 0.25% | emulsifier |
| deionized water | Q.S. | Q.S. | solvent, carrier |
| disodium EDTA | 0.05% | 0.05% | chelator |
| hydroxypropylmethylcellulose | 0.20% | 0.20% | film former |
| glycerin | 4.00% | 4.00% | humectant |
| butylene glycol | 2.00% | 2.00% | humectant, solvent |
| phenoxyethanol & parabens | 0.50% | 0.50% | preservative |
| triethanolamine | 0.45% | 0.45% | neutralizer |

After following the protocol described above in Example 1, the following results were obtained:

| | Formula A | Formula B |
|---|---|---|
| Average loss of UV-A | 26.33% | 22.36% |
| Average loss of UV-B | 25.15% | 18.29% |
| Average loss of SPF | 26.82% | 20.35% |

The test demonstrated that the naphthalene dicarboxylic acid derived polyester is comparable to octocrylene in its ability to photostabilize PARSOL® 1789.

Example 3

The following example is a preferred formulation for topical application to human hair to impart hair gloss and to stabilize natural and synthetically dyed hair from fading:

HAIR GLOSS AND HAIR COLOR STABILIZATION WITH DIETHYLHEXYL NAPHTHALATE

| | Chemical Name | Trade Name | % w/w |
|---|---|---|---|
| A | Polyacrylamide (&) C13–14 Isoparaffin (&) Laureth-7 | Sepigel 305 (Seppic) | 1.50 |
| A | Propylene glycol | | 40.00 |
| B | Phenoxyethanol | Sepicide LD (Seppic) | 1.00 |
| B | Fragrance | | 0.20 |
| B | Color | Dichrona RG + Dichrona GY (Merck) | q.s. |
| B | Water | | q.s. 100.00 |
| C | Cyclomethicone | DC345 (Dow Corning) | 11.20 |
| C | Diethylhexyl naphthalate | RX 13752 (C. P. Hall) | 2.80 |
| C | Cyclomethicone (&) Dimethiconol | Q2/1401 (Dow Corning) | 0.10 |

Procedure
1. Combine "A" ingredients carefully.
2. Add "B" ingredients in order shown.
3. Pre-mix "C" ingredients. Add to "A" plus "B".

What is claimed is:

1. A composition having an SPF of at least 2, for topical application to hair, in a cosmetically acceptable carrier, comprising at least about 0.1% by weight of a diester or polyester of naphthalene dicarboxylic acid selected from the group consisting of formula (I), formula (II), formula (III) and mixtures thereof:

(I)

(II)

(III)

wherein each $R^1$, same or different, is selected from the group consisting of an alkyl group having 1 to 22 carbon atoms; a diol having the structure HO—$R^2$—OH; and a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof.

2. A composition in accordance with claim 1, further including a dibenzoylmethane derivative in an amount of at least 0.5% by weight, and wherein the molar ratio of said diester or polyester compound having formula (I), (II) or (III) to said dibenzoylmethane derivative is about 0.1:1 to about 10:1.

3. A composition in accordance with claim 2, wherein the molar ratio of said diester or polyester compound having formula (I), (II) or (III) to said dibenzoylmethane derivative is about 0.1:1 to about 0.3:1.

4. A composition in accordance with claim 3, wherein said dibenzoylmethane derivative is selected from the group consisting of 4-(1,1-dimethylethyl)-4'-methoxydibenzoylmethane; 4-isopropyl dibenzoylmethane; and mixtures thereof.

5. A composition in accordance with claim 4, wherein the dibenzoylmethane derivative is 4-(1,1-dimethylethyl)-4'-methoxydibenzoylmethane.

6. A composition in accordance with claim 5, wherein the dibenzoylmethane derivative is included in the composition in an amount of about 0.5% to about 5% by weight of the composition.

7. A composition in accordance with claim 6, wherein the dibenzoylmethane derivative is included in the composition in an amount of about 0.5% to about 3% by weight of the composition.

8. A composition in accordance with claim 1, wherein the diester or polyester compound is included in the composition in an amount of about 0.1% to about 20% by weight of the composition.

9. A composition in accordance with claim 7, wherein the diester or polyester compound is a polyester of 2,6-naphthalene dicarboxylic acid.

10. A method of stabilizing the color of natural or synthetic dye-containing hair comprising topically applying to said hair a composition, in a cosmetically acceptable carrier, comprising 0.1% to 20% by weight of a diester or polyester of a naphthalene dicarboxylic acid stabilizing compound selected from the group consisting of formula (I), formula (II) and mixtures thereof:

wherein each $R^1$, same or different, is selected from the group consisting of an alkyl group having 1 to 22 carbon atoms; a diol having the structure $HO-R^2-OH$; and a polyglycol having the structure $HO-R^3-(-O-R^2-)_m-OH$, wherein $R^2$ and $R^3$, same or different, are each an alkylene group, straight chain or branched, having 1 to 6 carbon atoms, and wherein m and n are each in the range of 1 to about 100, or a mixture thereof.

11. A method in accordance with claim 10, wherein the composition includes a dibenzoylmethane derivative in an amount of about 0.5% to about 5%, and wherein the molar ratio of said diester or polyester compound having formula (I), (II) or (III) to said dibenzoylmethane derivative is about 0.1:1 to about 10:1.

12. A method in accordance with claim 11, wherein the molar ratio of said diester or polyester compound having formula (I), (II) or (III) to said dibenzoylmethane derivative is about 0.1:1 to about 0.3:1.

13. A method in accordance with claim 12, wherein said dibenzoylmethane derivative is selected from the group consisting of 4(1,1-dimethylethyl)-4'-methoxydibenzoylmethane; 4-isopropyl dibenzoylmethane; and mixtures thereof.

14. A method in accordance with claim 13, wherein the dibenzoylmethane derivative is 4-(1,1-dimethylethyl)-4'-methoxydibenzoylmethane.

15. A method in accordance with claim 14, wherein the dibenzoylmethane derivative is included in the composition in an amount of about 0.5% to 3% by weight of the composition.

16. A method of imparting gloss to human hair comprising topically applying to said hair, in a carrier, a diester or polyester of a naphthalene dicarboxylic acid compound selected from the group consisting of formula (I), formula (II), formula (III) and mixtures thereof:

wherein each $R^1$, same or different, is selected from the group consisting of an alkyl group having 1 to 22 carbon atoms; a diol having the structure $HO-R^2-OH$; and a polyglycol having the structure $HO-R^3-(-O-R^2-)_m-OH$, wherein $R^2$ and $R^3$, same or different, are each an alkylene group, straight chain or branched, having 1 to 6 carbon atoms, and wherein m and n are each in the range of 1 to about 100, or a mixture thereof.

17. The method of claim 16, wherein the composition further includes a dibenzoylmethane derivative in an amount of at least 0.5% by weight.

18. The composition of claim 1, wherein the diester of naphthalene dicarboxylic acid is a compound of formula III, and wherein each $R^1$ is an ethylhexyl group.

19. The method of claim 10, wherein the diester of naphthalene dicarboxylic acid is a compound of formula III, and wherein each $R^1$ is an ethylhexyl group.

20. The method of claim 16, wherein the diester of naphthalene dicarboxylic acid is a compound of formula III, and wherein each $R^1$ is an ethylhexyl group.

* * * * *